(12) United States Patent
Bolmström et al.

(10) Patent No.: US 6,843,474 B2
(45) Date of Patent: Jan. 18, 2005

(54) METHOD AND DEVICE FOR APPLICATION OF THIN OBJECTS

(75) Inventors: Anne Bolmström, Åkersberga (SE); Dusan Kolar, Knivsta (SE)

(73) Assignee: AB Biodisk, Solna (SE)

( * ) Notice: Subject to any disclaimer, the term of this patent is extended or adjusted under 35 U.S.C. 154(b) by 0 days.

(21) Appl. No.: 10/146,950

(22) Filed: May 17, 2002

(65) Prior Publication Data

US 2002/0185805 A1 Dec. 12, 2002

(30) Foreign Application Priority Data

May 17, 2001 (SE) .............................................. 0101740

(51) Int. Cl.[7] ................................................. B65H 5/08
(52) U.S. Cl. ...................... 271/11; 271/104; 271/107; 221/211
(58) Field of Search .......................... 271/11, 104, 107; 221/211

(56) References Cited

U.S. PATENT DOCUMENTS

| | | | | |
|---|---|---|---|---|
| 3,090,523 | A | * | 5/1963 | Packman ...................... 221/36 |
| 3,822,024 | A | * | 7/1974 | Endter et al. ............. 414/796.6 |
| 4,921,237 | A | * | 5/1990 | Nubson et al. ................ 271/11 |
| 5,106,260 | A | * | 4/1992 | Obrecht ................... 414/796.6 |
| 5,180,156 | A | * | 1/1993 | Matsui et al. ................ 271/103 |
| 5,433,426 | A | * | 7/1995 | Bond ............................ 271/92 |
| 5,967,508 | A | * | 10/1999 | Olexy ......................... 271/106 |
| 5,967,509 | A | * | 10/1999 | Rasimus et al. ............ 271/167 |
| 6,260,695 | B1 | * | 7/2001 | Tasber et al. ................ 206/5.1 |
| 6,534,017 | B1 | | 3/2003 | Bottwein et al. |
| 2002/0185806 | A1 | * | 12/2002 | Dettman et al. ............ 271/104 |

FOREIGN PATENT DOCUMENTS

| | | | |
|---|---|---|---|
| DE | 197 15031 A1 | 10/1998 | |
| EP | 0 064 691 A1 | 11/1982 | |
| EP | 0 259 283 A1 | 3/1988 | |
| EP | 0 722 089 A2 | 7/1996 | |
| JP | 54122570 A * | 9/1979 | ............ B65H/3/08 |
| JP | 02178118 A * | 7/1990 | ............ B65H/1/26 |
| JP | 02182638 A * | 7/1990 | ............ B65H/3/56 |
| JP | 02188327 A * | 7/1990 | ............ B65H/3/08 |
| JP | 04012941 A * | 1/1992 | ............ B65H/3/08 |
| JP | 05123791 A * | 5/1993 | ............ B21D/43/24 |
| JP | 06009091 A * | 1/1994 | ............ B65H/3/56 |
| WO | WO 98/47007 A1 | 10/1998 | |

* cited by examiner

*Primary Examiner*—Donald P. Walsh
*Assistant Examiner*—Matthew J. Kohner
(74) *Attorney, Agent, or Firm*—Birch, Stewart, Kolasch & Birch, LLP

(57) ABSTRACT

The present invention relates to a method of and an apparatus for separation and application of thin objects of a non-porous material or of a material of low porosity on a surface. The invention also relates to a package for the thin objects. With the aid of a pick up and lay down head on an application means a vacuum is applied on a part, preferably the middle, of the uppermost object in a stack of thin objects being in a recess of a package. The recess of the package for receiving the objects is at least areawise somewhat smaller than the exterior dimensions of the objects. With the aid of vacuum in the pick up and lay down head the uppermost object is lifted out of the package. The underlying objects in the stack remain in the package by the friction and scrape effects towards the interior walls of the package. Then the pick up and lay down head of the application means is lowered down so that the object is brought into contact with the surface.

11 Claims, 3 Drawing Sheets

METHOD AND DEVICE FOR APPLICATION OF THIN OBJECTS

PRIORITY APPLICATIONS

The present application claims priority under 35 U.S.C. § 119(a–d) of Swedish application 010740-9, filed May 17, 2001.

CROSS-REFERENCE TO RELATED DOMESTIC APPLICATIONS

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISK

Not applicable.

BACKGROUND OF THE INVENTION

The present invention relates to a method of separation and application of thin objects of a non-porous material or of a material of low porosity on a surface for biological and/or chemical reactions. The invention further relates to an apparatus for automatic separation and application of these objects and a package for the thin objects.

To determine various substances' ability of inhibiting or promoting growth of e.g. a microorganism, the substances are applied on a cultivation surface for the organism. This is accomplished by applying a carrier on the cultivation surface, on which carrier one or more substances are present in a predetermined and defined concentration pattern. Then the substances diffuse into the cultivation surface, e.g. agar, and the desired concentration pattern of substance(s) is achieved in the cultivation medium. After incubation of the cultivation medium with the substance and the microorganism to be tested, the result is normally read by measuring the inhibition zone. Various examples of how to perform this is illustrated i.a. in EP 0 157 071 and EP 0 444 390. These patents describe how to transfer a predetermined and defined concentration pattern of substances with the aid of thin, rectangular or square carriers having the substance(s) in the predetermined concentration pattern. These carriers, also called test strips, are very thin and made of a non-porous material or a material of low porosity, e.g. some kind of plastic material. They are applied manually on the cultivation surface as it has been difficult to achieve a more automated separation and application. So far these strips have been packed in stacks in blister packs of some suitable plastic material with smooth interior walls and of a dimension somewhat larger than that of the test strips. When picking up the uppermost strip from such a package it is difficult to pick up only that one without picking up a number of underlying strips due to adherence e.g. by static electricity.

U.S. Pat. No. 5,026,039 describes a method of feeding sheets from a stack of sheets in e.g. a copying machine using vacuum to lift the uppermost sheet. During the feeding a leaf spring is adapted in the paper path to separate the uppermost sheet from the subsequent sheet so that only one sheet is fed at the time.

SUMMARY OF THE INVENTION

Not applicable.

BRIEF DESCRIPTION OF THE SEVERAL VIEWS OF THE DRAWINGS

The invention is closer described in the following non-limiting embodiments illustrated on the enclosed drawings. In the embodiment shown the thin objects are rectangular.

DETAILED DESCRIPTION OF THE INVENTION

Figure 1:
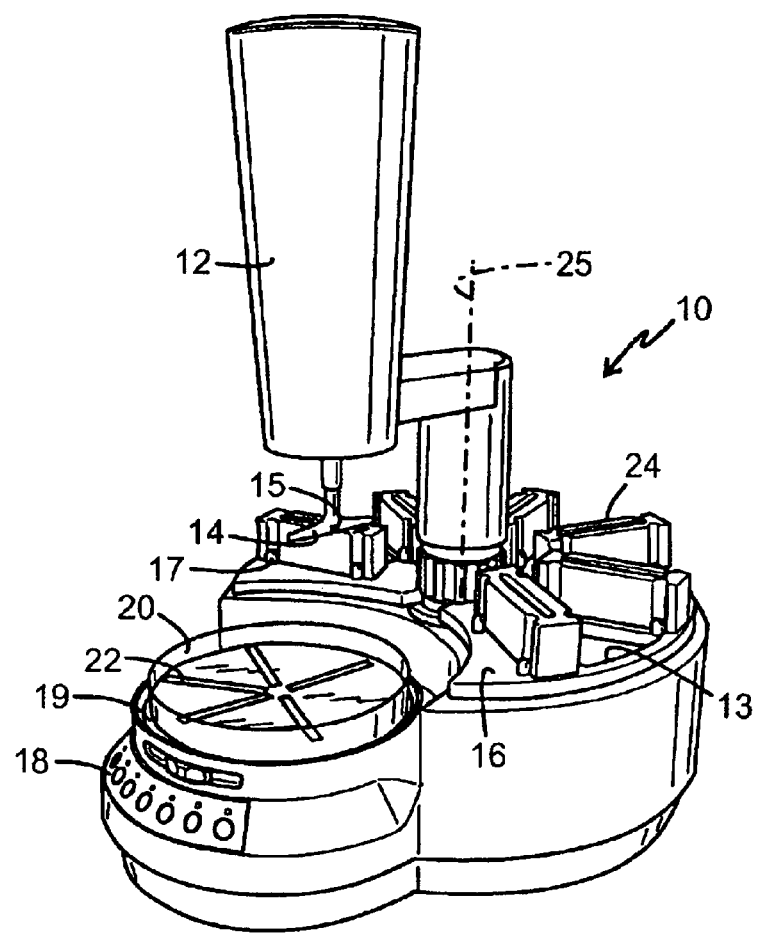
FIG. 1 shows an embodiment of an apparatus of the invention.

The present invention relates to a method of separation and application of thin objects of non-porous material or a material of low porosity on a surface for biological and/or chemical reactions. One example on such a surface to be mentioned is that of a cultivation medium, e.g. a surface of agar or agarose. On the side of the thin objects that shall be applied towards the surface there may be a predetermined and defined concentration pattern of chemically or biologically active substances. The shape of the thin objects is non-limiting and they may be e.g. rectangular, square, oval or circular. By a pick up and lay down head on an application means vacuum is applied on a part, preferably the middle, of the uppermost object in a stack of the thin objects in a package. A recess of the package for receiving the objects is at least areawise somewhat smaller than the exterior dimensions of the objects. With the aid of the vacuum in the pick up and lay down head the uppermost object is lifted out of the package. By the friction and scrape effects against the interior walls of the package the uppermost of the thin objects will during the lifting movement attain a convex shape. However, the underlying objects of the stack will be retained in the package with the aid of a friction and scrape effect against its interior walls. Thereafter the object is applied on the surface by lowering the pick up and lay down head of the application means so that the contact between the object and the surface is maximized.

The expression biological and/or chemical reactions comprises those mentioned in EP 0 157 071 and EP 0 444 390.

In one embodiment the packages are applied on a rotateable disc. The desired package is put into position under the pick up and lay down head by rotating the disc, whereafter the uppermost object is lifted out of the package. Thereafter the rotateable disc is turned back into its original position and the object is applied on the surface by lowering the pick up and lay down head. Then another package is brought into position under the pick up and lay down head and the next object is lifted up with the aid of the pick up and lay down head. Then the rotateable disc is turned back into its original position and the object is applied on the surface. It is continued in this way until the desired number of objects has been applied on predetermined spots on the surface.

In another embodiment the rotateable disc has openings between the packages to allow the lowering of the pick up and lay down head to the surface. In this embodiment the desired package is brought in a position under the pick up and lay down head, the uppermost object is lifted out of the package and the rotateable disc is turned so that the pick up and lay down head is brought into position above the closest opening in the disc. Thereafter the object is applied on the surface by lowering the pick up and lay down head through the opening.

In still another embodiment it is the application means that is turned so that the pick up and lay down head is brought into position above the package from which an object is to be picked up. By the pick up and lay down head the object is removed from the package, whereafter the application means is turned into a position above the surface on which the object is to be applied. Thereafter the object is applied on the surface by lowering the pick up and lay down head. Then the application means is turned so that it comes into position above the next desired package. The uppermost object in this package is picked up, the application means is turned back into position above the surface and the object is applied thereon. It is continued in this way until the desired number of objects have been applied on predetermined spots on the surface.

In one embodiment of the invention the thin objects are applied in a predetermined order and on predetermined spots of the surface.

Non-limiting examples on non-porous material or material of low porosity are plastics, such as polyacrylamide, polyester, polyamide, polycarbonate or similar material.

The present invention also concerns an apparatus for separation and application of thin objects of a non-porous material or a material of low porosity on a surface for biological and/or chemical reactions. The shape of the thin objects is non-limiting, and they can e.g. be rectangular, square, oval or circular. The apparatus comprises one or more holders for packages for the thin objects, which holders are applied on a rotateable disc, and an application means having a pick up and lay down head that can be lifted and lowered. This head is designed to be lowered into the recess of a package, and it is flexibly suspended in the application means. The disc can be rotated from its original position so that each of the packages can be brought into a position below the pick up and lay down head. On the pick up and lay down head a vacuum may be applied or released to pick up the uppermost object in the package and apply it on the surface, respectively. The apparatus further comprises a holder for the surface on which the object is to be applied. The holder is rotateable and when an object is applied on the surface and the pick up and lay down head has been raised to fetch a new object from the package, the holder is rotated and thereby the surface so that the next object is applied on another spot on the surface.

A driving device is connected to the rotateable disc to move it in a predetermined moving scheme. Another driving device is connected to the rotateable holder for the surface on which the objects are to be applied. In this way the apparatus can be set so that it lifts the thin objects one by one from the packages in a predetermined order and applies them on predetermined positions on the surface.

One embodiment of the present invention concerns an apparatus comprising one or several holders for packages of the thin objects, which holders are applied on a disc, an application means being rotateable around an axis and having a pick up and lay down head that may be lifted up and lowered down. This head is so designed that it can be lowered into the recess and is flexibly suspended in the application means. On the pick up and lay down head a vacuum can be applied or released for lifting up the uppermost object in the package, its separation from the other objects of the package and its application on the surface, respectively. The apparatus further comprises a rotateable holder for the surface on which the objects are to be applied.

A driving device is connected to the application means to move this along a predetermined moving scheme. Another driving device is connected to the rotateable holder for the surface on which the objects are to be applied. In this way the complete apparatus can be set so that it lifts the thin objects one by one from the packages in a predetermined order and applies them on predetermined positions on the surface.

The shape of the pick up and lay down head is not limiting and it may be e.g. rectangular, square, oval or circular. A channel extends in the middle of the pick up and lay down head through which a vacuum may be applied.

Further the invention concerns a package for thin objects of non-porous material or material of low porosity. The shape of the thin objects is non-limiting, and they may be e.g. rectangular, square, oval or circular. The package is of a soft, bendable material with a recess for receiving the objects, which recess at least areawise, is somewhat smaller than the exterior dimensions of the objects.

In one shown embodiment of the invention the recess for receiving of objects in the package is in its width somewhat smaller than the width of the objects.

The package may be of any shape, the essential thing is that the recess at least areawise is somewhat smaller than the exterior dimensions of the objects. Examples of suitable material for the packages are foamed plastic, cellular plastic, expanded rubber and foamed rubber with open or closed cells with or without a crosslinked molecular structure. Examples of such materials are low or high density polyethene, polypropene, vinyl plastic, polystyrene, polyurethane and the like. When removing an object from the package the rough wall rims of the cells in the recess of the package create an irregular friction against the objects. A consequence of this is that the uppermost object is lifted out of the package while the underlying objects of the stack remain in the package.

In one preferred embodiment the packages may have a bottom of a somewhat stiffer material, which facilitates the handling. The material in the bottom may be the same as in the other parts of the package, but in embodiments with a stiffer material in the bottom this material has a higher density than that of the other part of the package.

FIG. 1 shows an apparatus 10 with application means 12 for separation and application of thin objects of non-porous material or material of low porosity on a surface for biological and/or chemical reactions, such as the surface of a cultivation medium. The apparatus 10 comprises a holder 17 for packages 24 of the thin objects. The packages are exchangeable. These holders 17 are applied on a rotateable disc 16. In the disc 16 there are openings 13 between the surfaces that are occupied by the packages 24. The disc rotates around an axis 25. A pick up and lay down head 14 that can be lifted up and lowered down is flexibly suspended in the application means 12. In the middle of the pick up and lay down head is a channel 15, through which a vacuum can be applied. The disc 16 is connected to a driving device (not shown) and the apparatus 10 can with the aid of the panel 18 be set so that it lifts the objects out of the packages 24 in a predetermined order. Further the apparatus 10 comprises a rotateable holder 19 for the surface on which the thin objects 22 are applied. In the embodiment shown it is an agar surface in a Petri dish 20. The holder 19 is connected to a driving device (not shown).

Figure 2:
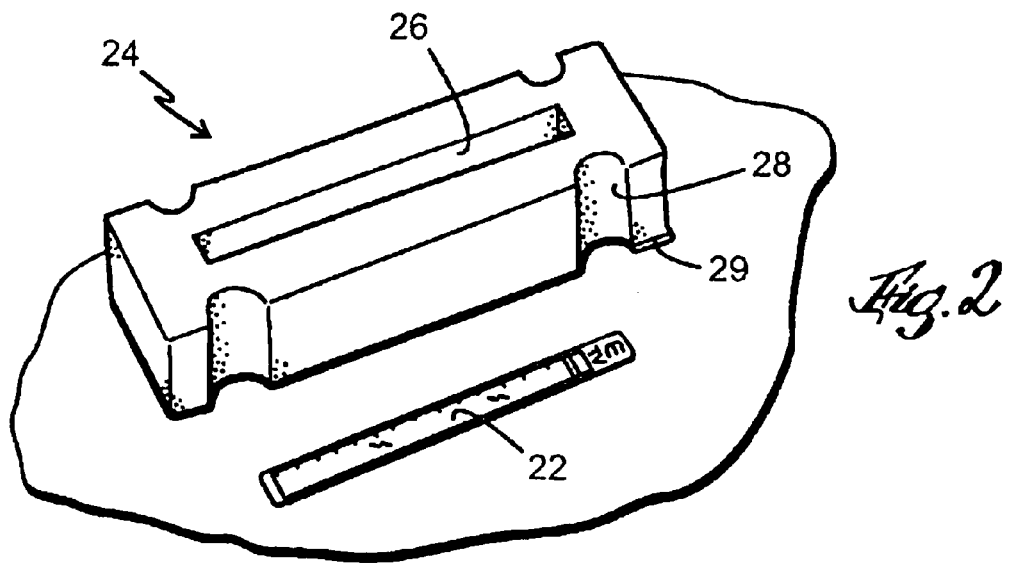
FIG. 2 shows an embodiment of the package of the invention.

FIG. 2 shows an embodiment of a package 24 for thin objects 22 of non-porous material or a material of low porosity having a predetermined and defined concentration pattern of chemically or biologically active compounds on one side of the object. The package 24 with a bottom 29 has a recess 26 for receiving the objects 22 and recesses 28 for the holders 17 (in the apparatus 10 of FIG. 1).

Figure 3:
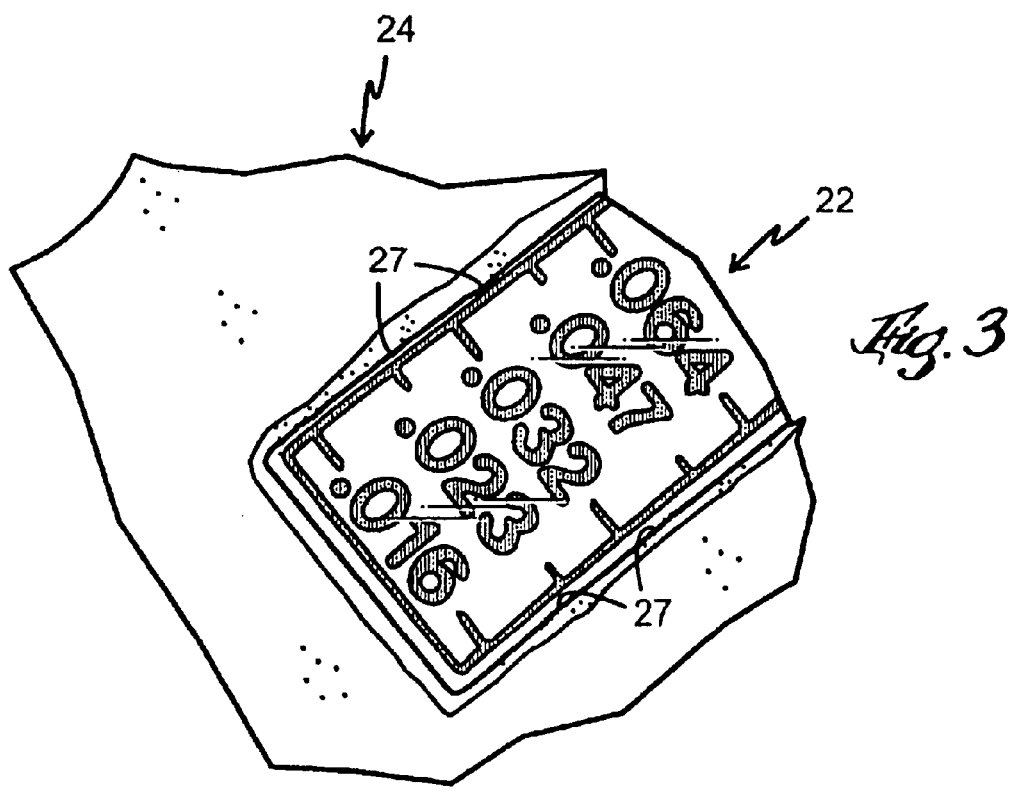
FIG. 3 shows in enlargement a part of the package and FIG. 4 shows one step of the process of the invention.

FIG. 3 shows in enlargement a part of the package 24 and the object 22 (with a concentration scale) in the recess 26. The parts of the longitudal walls of the recess that will come into contact with the longitudal rims of the object are designated 27.

Figure 4:
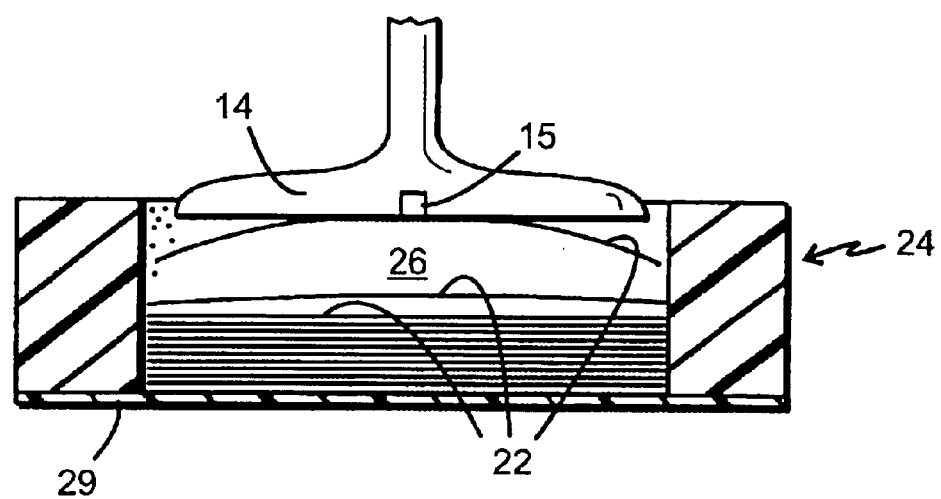

FIG. 4 shows a cross section of a package 24 with a number of thin objects 22. In a pick up and lay down head 14 a vacuum has been applied through a channel 15. In the figure is shown how the pick up and lay down head 14 on its way up from the recess 26 of the package 24 brings the uppermost of the thin objects 22 while the others remain in the package due to the friction and scrape effects towards the interior walls of the package 24.

What is claimed is:

1. An apparatus for separation and application of thin objects of a non-porous material or of a material of low porosity on a surface for biological and/or chemical reactions comprising one or more holders (17) for packages (24) of thin objects (22), which holders are applied on a rotateable disc (16), an application means (12) with a pick up and lay down head (14) being designed so that it can be lowered down into a recess (26) in a package (24) and being flexibly suspended in the application means (12), the pick up and lay down head (14) can be lifted up and lowered down, and through the pick up and lay down head (14) a vacuum can be applied or released for the picking up of the uppermost object (22) in the package (24) for its separation and application on the surface, respectively, and a rotateable holder (19) for the surface on which the object is to be applied.

2. The apparatus of claim 1, in which a channel (15) extends through the pick up and lay down head (14) through which a vacuum can be applied.

3. The apparatus of claim 1 or 2, further comprising a first driving device reconnected to the rotateable disc (16) to move the rotatable disc in a predetermined moving scheme and a second driving device connected to the rotateable holder (19) for the surface on which the object is to be applied, so that the apparatus (10) can be set to pick the thin objects (22) one by one from the packages (24) in a predetermined order and apply them on predetermined positions on the surface.

4. A method for separating thin objects made of a non-porous material or of a material of low porosity and applying them to a surface comprising separating said thin objects using the apparatus of claim 1 and applying them to a surface using the apparatus of claim 1.

5. The method of claim 4, in which a stack of thin objects is separated and the separating and applying comprises a step of applying a vacuum to the middle portion of the uppermost object in the stack.

6. The method of claim 4, in which the thin objects are applied to the surface in a predetermined way and at predetermined locations on the surface.

7. The method of any one of claims 4–6, in which there is a predetermined and defined concentration pattern of at least one chemically or biologically active substance on the side of the object that is to be applied to the surface.

8. A method for separating thin objects made of a non-porous material or of a material of low porosity and applying them to a surface comprising selecting said thin objects one-by-one from a package in a predetermined order using the apparatus of claim 3 and applying them to a predetermined position on the surface using the apparatus of claim 3.

9. An apparatus for separation and application of thin objects of a non-porous material or of a material of low porosity on a surface for biological and/or chemical reactions comprising one or more holders (17) for packages (24) of the thin objects (22), an application means (12) being rotateable around an axis and having a pick up and lay down head (14) which is designed to be lowered into a recess (26) of a package (24) and is flexibly suspended in the application means (12), and the pick up and lay down head (14) can be lowered down or lifted up and a vacuum can be applied or released through the pick up and lay down head (14) to lift up the uppermost object (22) in the package (24), separate it from the other objects in a stack and apply it on the surface, respectively, and a rotateable holder (19) for the surface on which the object is to be applied.

10. The apparatus of claim 9, in which a channel (15) extends through the pick up and lay down head (14) through which a vacuum can be applied.

11. The apparatus of claim 9 or 10, further comprising a first driving device connected to the application means (12) to move the application means in a predetermined moving scheme and a second driving device connected to the rotateable holder (19) for the surface on which the object is to be applied, so that the apparatus (10) can be set to pick the thin objects (22) one by one from the packages (24) in a predetermined order and apply them on predetermined positions on the surface.

* * * * *